(12) United States Patent
Hartle et al.

(10) Patent No.: US 8,375,630 B2
(45) Date of Patent: Feb. 19, 2013

(54) METHOD TO IMPROVE GERMINATION OF EMBRYOS FROM MANUFACTURED SEED

(75) Inventors: Jeffrey E. Hartle, Tacoma, WA (US); William C. Carlson, Olympia, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 115 days.

(21) Appl. No.: 12/874,080

(22) Filed: Sep. 1, 2010

(65) Prior Publication Data

US 2011/0072716 A1    Mar. 31, 2011

Related U.S. Application Data

(60) Provisional application No. 61/247,354, filed on Sep. 30, 2009.

(51) Int. Cl.
*A01C 1/06* (2006.01)
(52) U.S. Cl. ........................................ 47/57.6
(58) Field of Classification Search .............. 47/57.6, 47/58.1 R, 58.1 SE, 61
See application file for complete search history.

(56) References Cited

U.S. PATENT DOCUMENTS

| | | | |
|---|---|---|---|
| 2,671,985 A * | 3/1954 | Vogelsang | 504/100 |
| 6,119,395 A | 9/2000 | Hartle et al. | |
| 7,568,309 B2 | 8/2009 | Hirahara | |
| 2003/0167684 A1* | 9/2003 | Carlson et al. | 47/57.6 |
| 2005/0108936 A1* | 5/2005 | Hartle et al. | 47/57.6 |
| 2005/0108937 A1* | 5/2005 | Hirahara | 47/57.6 |
| 2005/0150161 A1 | 7/2005 | Hartle et al. | |
| 2006/0064930 A1 | 3/2006 | Carlson et al. | |
| 2007/0283621 A1* | 12/2007 | Holloway | 47/56 |

FOREIGN PATENT DOCUMENTS

| | | |
|---|---|---|
| CA | 2699899 | 4/2009 |
| EP | 373348 A2 * | 6/1990 |
| WO | 9926470 A1 | 6/1999 |

* cited by examiner

*Primary Examiner* — Rob Swiatek
*Assistant Examiner* — Ebony Evans
(74) *Attorney, Agent, or Firm* — Woodcock Washburn LLP (57) ABSTRACT

The invention provides methods for improving germination of manufactured seeds. The manufactured seed of the invention comprises a seed coat, nutritive media comprising an adsorbent material in a concentration from about 30 g/L to about 100 g/L, and a shoot restraint comprising a cavity. The manufactured seed further comprises a plant embryo. The adsorbent material may be nutrient-treated or non-nutrient-treated charcoal. The manufactured seed may optionally contain an adsorbent material in the cavity of the shoot restraint.

20 Claims, 5 Drawing Sheets

METHOD TO IMPROVE GERMINATION OF EMBRYOS FROM MANUFACTURED SEED

CROSS-REFERENCE(S) TO RELATED APPLICATION(S)

The present application claims the benefit of U.S. Provisional Application No. 61/247,354 filed Sep. 30, 2009.

FIELD OF THE INVENTION

The present invention relates to methods for improving germination of embryos from manufactured seed.

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant. Plant embryos created by in vitro cultures, however, lack the natural protective and nutritive features of natural botanic seeds. Attempts have been made to provide the protective and nutritive structures found in natural botanic seeds to plant embryos cultured in a laboratory by using manufactured seeds. Manufactured seeds are described, for example, in U.S. Pat. Nos. 5,564,224; 5,687,504; 5,701,699; and 6,119,395. Problems with manufactured seeds remain. Both the rate of successful germination and the quality of germinants produced from manufactured seeds are lower than the rate and quality obtained from natural botanic seeds. Therefore, there is a need to improve the rate of germination and the quality of germinants obtained from manufactured seeds. The present invention addresses these and other needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present invention provides a manufactured seed comprising (a) a seed coat; (b) a nutritive media comprising an adsorbent material, wherein the adsorbent material is present in the media in a concentration from about 30 g/L to about 100 g/L; and (c) a shoot restraint, wherein the shoot restraint comprises a cavity. In one embodiment, the manufactured seed further comprises a plant embryo disposed in the cavity of the shoot restraint. In one embodiment, the adsorbent material in the nutritive media is charcoal. In one embodiment, the adsorbent material in the nutritive media is nutrient-treated charcoal.

In one embodiment, the shoot restraint further comprises an adsorbent material within the cavity. In one embodiment, the adsorbent material in the cavity is charcoal. In one embodiment, the adsorbent material within the cavity is nutrient-treated charcoal.

In another aspect, the present invention provides methods for improving the germination of a plant embryo from a manufactured seed. In one embodiment, the method comprises the steps of (a) assembling a manufactured seed comprising a seed coat and a shoot restraint, wherein the shoot restraint comprises a cavity; (b) adding nutritive media comprising an adsorbent material, wherein the adsorbent material is present in the media in a concentration from about 30 g/L to about 100 g/L, to the seed coat; (c) placing a plant embryo into the cavity of the shoot restraint; and (d) culturing the manufactured seed under conditions suitable for germination of the plant embryo.

In one embodiment, the method comprises the steps of (a) assembling a manufactured seed comprising a seed coat and a restraint, wherein the restraint comprises a cavity; (b) adding nutritive media comprising an adsorbent material, wherein the adsorbent material is present in the media in a concentration from about 30 g/L to about 100 g/L, to the seed coat; (c) placing a plant embryo into the cavity of the restraint; (d) adding an adsorbent material to the cavity; and (e) culturing the manufactured seed under conditions suitable for germination of the plant embryo.

It is to be understood that the order of the steps in the method may be altered without departing from the scope of the invention. For example, an adsorbent material can be placed into the cavity of the restraint before the embryo is placed into the restraint.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Unless specifically defined herein, all terms used herein have the same meaning as they would to one skilled in the art of the present invention.

Unless stated otherwise, all concentration values that are expressed as percentages are weight per volume percentages.

In one aspect, the present invention provides a manufactured seed comprising (a) a seed coat; (b) a nutritive media comprising an adsorbent material, wherein the adsorbent material is present in the media in a concentration from about 30 g/L to about 100 g/L (such as, for example, from about 50 g/L to about 100 g/L, from about 60 g/L to about 100 g/L, or from about 75 g/L to about 100 g/L); and (c) a shoot restraint, wherein the shoot restraint comprises a cavity. In one embodiment, the manufactured seed further comprises a plant embryo.

Figure 1:
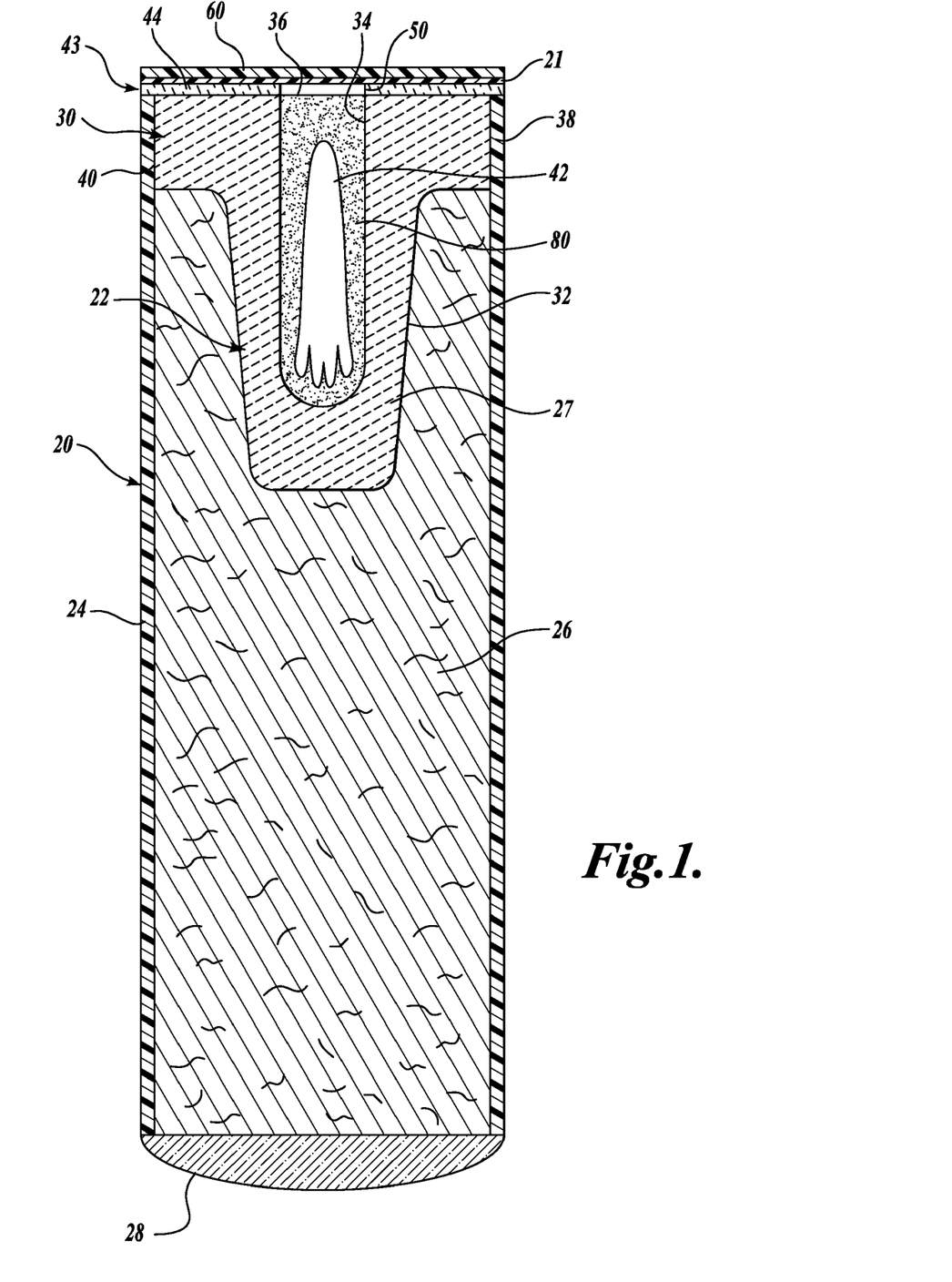
FIG. 1 is a side cross-sectional planar view of an exemplary manufactured seed comprising an embryo for use in the methods of the present invention.

FIG. 1 is a side cross-sectional planar view of an exemplary manufactured seed 20 comprising a plant embryo 42 disposed within. As shown in FIG. 1, the embryo 42 is disposed within a cavity 34, is in functional contact with nutritive media 26, and is suitably sealed therein by a live end seal 43. It will be understood that FIG. 1 provides a representative embodiment of a manufactured seed 20; however, the method of the invention is not limited to the particular embodiment of the manufactured seed shown in FIG. 1. In the exemplary embodiment shown in FIG. 1, the manufactured seed 20 comprises a seed coat 24, nutritive media 26, a dead end seal 28, and an optional shoot restraint 22.

As used herein, a "seed coat" refers to a structure analogous to a natural seed coat that protects the plant embryo and other internal structures of the manufactured seed from mechanical damage, desiccation, from attack by microbes, fungi, insects, nematodes, birds, and other pathogens, herbivores, and pests, among other functions. The seed coat 24 may be fabricated from a variety of materials including, but not limited to, cellulosic materials, glass, plastic, moldable plastic, cured polymeric resins, paraffin, waxes, varnishes, and combinations thereof such as a wax-impregnated paper. The materials from which the seed coat is made are generally non-toxic and provide a degree of rigidity. The seed coat can be biodegradable, although typically the seed coat remains intact and resistant to penetration by plant pathogens until after emergence of the germinating embryo. The seed coat may be formed from a section of tubular material. The seed coat may be a sectioned straw of fibrous material, such as paper. The sections of straw may be pretreated in a suitable coating material, such as wax. Alternatively, the seed coat may be formed from a tubular section of biodegradable, plastic material. One such material is polylactic acid ("PLA") and is sold by NAT-UR of Los Angeles, Calif. Another suitable material is a polycaprolactone ("PCL") mixture, such as CAPA 6800 (Perstorp Polyols Inc., Toledo, Okla. 43612) with or without a 1% Tegomer H SI6440 plasticizer (Degussa Goldschmidt Chemical Corp, 914 East Randolph Road, Hopewell, Va. 23860). Such biodegradable plastic tubes may or may not require a wax coating as such tubes are already resistive to environmental elements. Additives such as antibiotics and plant-growth regulators may be added to the seed coat, for example, by incorporation into the material forming one or more of the layers of the seed coat or by coating or otherwise treating the layer(s) with the additive by conventional means.

In accordance with the manufactured seeds and methods of the invention, nutritive media 26 is in functional contact with the plant embryo disposed within the manufactured seed 20. As used herein, a "nutritive media" refers to a source of nutrients, such as vitamins, minerals, carbon, and energy sources, and other beneficial compounds used by the embryo during germination. Thus, the nutritive media 26 is analogous to the gametophyte of a natural seed. A nutritive media 26 according to the invention may include a substance that causes the media to be a semi-solid or have a congealed consistency under normal environmental condition. Typically, the nutritive media 26 is in the form of a hydrated gel. A "gel" is a substance that is prepared as a colloidal solution and that will, or can be caused to, form a semi-solid material. Such conversion of a liquid gel solution into a semi-solid material is termed herein "curing" or "setting" of the gel. A "hydrated gel" refers to a water-containing gel. Such gels are prepared by first dissolving in water (where water serves as the solvent or "continuous phase") a hydrophilic polymeric substance (serving as the solute or "disperse phase") that, upon curing, combines with the continuous phase to form the semi-solid material. Thus, the water becomes homogeneously associated with the solute molecules without experiencing any substantial separation of the continuous phase from the disperse phase. However, water molecules can be freely withdrawn from a cured hydrated gel, such as by evaporation or imbibition by a germinating embryo. When cured, these gels have the characteristic of compliant solids, like a mass of gelatin, where the compliance becomes progressively less and the gel becomes more "solid" to the touch as the relative amount of water in the gel is decreased.

In addition to being water-soluble, suitable gel solutes are neither cytotoxic nor substantially phytotoxic. As used herein, a "substantially non-phytotoxic" substance is a substance that does not interfere substantially with normal plant development, such as by killing a substantial number of plant cells, substantially altering cellular differentiation or maturation, causing mutations, disrupting a substantial number of cell membranes or substantially disrupting cellular metabolism, or substantially disrupting other process.

Candidate gel solutes include, but are not limited to, the following: sodium alginate, agar, agarose, amylose, pectin, dextran, gelatin, starch, amylopectin, modified celluloses such as methylcellulose and hydroxyethylcellulose, and polyacrylamide. Other hydrophilic gel solutes can also be used, so long as they possess similar hydration and gelation properties and lack of toxicity.

Gels are typically prepared by dissolving a gel solute, usually in fine particulate form, in water to form a gel solution. Depending upon the particular gel solute, heating is usually necessary, sometimes to boiling, before the gel solute will dissolve. Subsequent cooling will cause many gel solutions to reversibly "set" or "cure" (become gelled). Examples include gelatin, agar, and agarose. Such gel solutes are termed "reversible" because reheating cured gel will re-form the gel solution. Solutions of other gel solutes require a "complexing" agent which serves to chemically cure the gel by crosslinking gel solute molecules. For example, sodium alginate is cured by adding calcium nitrate (Ca(NO3)2) or salts of other divalent ions such as, but not limited to, calcium, barium, lead, copper, strontium, cadmium, zinc, nickel, cobalt, magnesium, and iron to the gel solution. Many of the gel solutes requiring complexing agents become irreversibly cured, where reheating will not re-establish the gel solution.

The concentration of gel solute varies depending upon the particular gel solute. For example, a useful concentration of sodium alginate is within a range of about 0.5% w/v to about 2.5% w/v, preferably about 0.9% w/v to 1.5% w/v. A useful concentration of agar is within a range of about 0.8% w/v to about 2.5% w/v, preferably about 1.8% w/v. In general, gels cured by complexing require less gel solute to form a satisfactory gel than "reversible" gels.

The nutritive media 26 typically comprises one or more carbon sources, an adsorbent material, vitamins, and minerals. Suitable carbon sources include, but are not limited to, monosaccharides, disaccharides, and/or starches. Suitable adsorbent materials include, but are not limited to charcoal, polyvinyl polypyrolidone, and silica gels. The nutritive media 26 may also comprise amino acids and a smoke suspension. Suitable amino acids may include amino acids commonly found incorporated into proteins as well as amino acids not commonly found incorporated into proteins, such as argininosuccinate, citrulline, canavanine, ornithine, and D-stereoisomers. A suitable smoke suspension contains one or more compounds generated through the process of burning organic matter, such as wood or other cellulosic material. Solutions containing these by-products of burning organic matter may be generated by burning organic matter, washing the charred material with water, and collecting the water. Solutions may also be obtained by heating the organic matter and condensing and diluting volatile substances released from such heating. Certain types of smoke suspensions may be purchased from commercial suppliers, for example, Wright's Concentrated Hickory Seasoning Liquid Smoke (B&G Foods, Inc. Roseland, N.J. 07068). Smoke suspension may be incorporated into the nutritive media 26 in any of various forms. For instance, smoke suspension may be incorporated as an aerosol, a powder, or as activated clay. An exemplary concentration of Wright's Concentrated Hickory Seasoning Liquid Smoke liquid smoke suspension, if present, is between 0.0001 ml and 1 ml of smoke suspension per liter of media. The nutritive media 26 may also include one or more compounds involved in nitrogen metabolism, such as urea or polyamines.

The nutritive media 26 may include oxygen-carrying substances to enhance both the absorption of oxygen and the retention of oxygen by the nutritive media 26, thereby allowing the media to maintain a concentration of oxygen that is higher than would otherwise be present in the media solely from the absorption of oxygen from the atmosphere. Exemplary oxygen-carrying substances include perfluorocarbons such as FC-77 (3M Corporation, St. Paul, Minn.), emulsified with a surfactant such as Pluronic F-68, available from BASF Corp., Parsippany, N.J. Exemplary oxygen-carrying substances are described in U.S. Pat. No. 5,564,224 (e.g., Col. 9, line 44, to Col. 11, line 67), herein incorporated by reference.

The nutritive media 26 may also contain hormones. Suitable hormones include, but are not limited to, abscisic acid, cytokinins, auxins, and gibberellins. Abscisic acid is a sesquiterpenoid plant hormone that is implicated in a variety of plant physiological processes (see, e.g., Milborrow, *J. Exp. Botany* 52:1145-1164 (2001); Leung & Giraudat *Ann. Rev. Plant Physiol. Plant Mol. Biol.* 49:199-123 (1998)). Auxins are plant growth hormones that promote cell division and growth. Exemplary auxins for use in the germination media include, but are not limited to, 2,4-dichlorophenoxyacetic acid, indole-3-acetic acid, indole-3-butyric acid, naphthalene acetic acid, and chlorogenic acid. Cytokinins are plant growth hormones that affect the organization of dividing cells. Exemplary cytokinins for use in the germination media include, but are not limited to, e.g., 6-benzylaminopurine, 6-furfurylaminopurine, dihydrozeatin, zeatin, kinetin, and zeatin riboside. Gibberellins are a class of diterpenoid plant hormones (see, e.g., Krishnamoorthy *Gibberellins and Plant Growth*, John Wiley & Sons, (1975)). Representative examples of gibberellins useful in the practice of the present invention include gibberellic acid, gibberellin 3, gibberellin 4, and gibberellin 7. An example of a useful mixture of gibberellins is a mixture of gibberellin 4 and gibberellin 7 (referred to as gibberellin 4/7), such as the gibberellin 4/7 sold by Abbott Laboratories, Chicago, Ill.

The nutritive media 26 may also include antimicrobials. Suitable antimicrobials are available from Sigma-Aldrich, St. Louis, Mo., sold as Product #A5955. Antimicrobials may be used, for example, at a concentration of 1 ml/L.

When abscisic acid is present in the nutritive media 26, it is typically used at a concentration in the range of from about 1 mg/L to about 200 mg/L. When present in the nutritive media 26, the concentration of gibberellin(s) is typically between about 0.1 mg/L and about 500 mg/L. Auxins may be used, for example, at a concentration of from 0.1 mg/L to 200 mg/L. Cytokinins may be used, for example, at a concentration of from 0.1 mg/L to 100 mg/L.

Exemplary nutritive media are described in U.S. Pat. No. 5,687,504 (e.g., Col. 8, line 63, to Col. 9, line 41) and in U.S. Patent Publication No. 2003/0167684, herein incorporated by reference. A representative nutritive media 26 is KE64-50, the composition of which is set forth in Table 1 below.

In one embodiment of the invention, the concentration of the adsorbent material in the nutritive media 26 is from about 30 g/L to about 100 g/L. In another embodiment, the concentration of the adsorbent material in the nutritive media 26 is from about 50 g/L to about 100 g/L. In another embodiment, the concentration of the adsorbent material in the nutritive media 26 is from about 60 g/L to about 100 g/L. In another embodiment, the concentration of the adsorbent material in the nutritive media 26 is from about 75 g/L to about 100 g/L. In one embodiment, the adsorbent material is charcoal. In one embodiment, the adsorbent material is nutrient-treated charcoal. As used herein, "nutrient-treated" charcoal refers to charcoal that has been treated with a media that contains a variety of nutrients, such as a carbon source, vitamins, minerals, and amino acids, so that the charcoal absorbs and retains nutrients from the media. A representative media used to prepare nutrient-treated charcoal is media KE64-50. A representative method for preparing nutrient-treated charcoal is described in Example 2.

The shoot restraint 22 of a manufactured seed is suitably manufactured from a porous material having a hardness strong enough to resist puncture or fracture by a germinating embryo, such as a ceramic or porcelain material, and includes an end seal portion 30 and a cotyledon restraint portion 32. The restraint portion 32 has an interior surface for contacting and surrounding at least the shoot end of a plant embryo and resists penetration by the shoot end during germination. The shoot restraint prevents the shoot end of the embryo, such as the cotyledons, from growing into and becoming entrapped in the nutritive media (also referred to as nutritive media). The cotyledon restraint portion 32 is suitably integrally or unitarily formed with the end seal portion 30. The shoot restraint 22 also includes a longitudinally extending cavity 34 extending through the end seal portion 30 and partially through one end of cotyledon restraint portion 32. The open end of the cavity 34 is known as a cotyledon restraint opening 36. The cavity 34 is sized to receive a plant embryo 42 therein. As shown in FIG. 1, the shoot restraint 22 comprises a plurality of pores 27, wherein the pores 27 allow the nutritive media 26 access into the inside of the cavity 34 comprising the embryo 42 and, therefore, allows the nutritive media 26 to functionally contact the embryo 42 under conditions sufficient to generate a conditioned embryo, as described herein.

The restraint is porous to allow access of the embryo to water, nutrients, and oxygen. The shoot restraint may be fabricated from any suitable material, including, but not limited to, glassy, metal, elastomeric, ceramic, clay, plaster, cement, starchy, putty-like, synthetic polymeric, natural polymeric, and adhesive materials. Exemplary shoot restraints are described in U.S. Pat. No. 5,687,504 (e.g., Col. 3, line 61, to Col. 4, line 13; Col. 18, line 7, to Col. 22, line 2), herein incorporated by reference.

All or only part of the plant embryo 42 may be inserted into the shoot restraint 22. Typically, at least the shoot end of the embryo is inserted into the shoot restraint 22. The surface area of nutrient uptake in a manufactured seed 20 is limited to the area of the plant embryo 42 that is in direct contact with the interior surface of the shoot restraint 22. During germination of plant embryos, the cotyledons have been found to be the primary organs for nutrient uptake (Brown & Gifford, *Plant Physiol.* 33:57-64 (1958)).

Either the interior surface of the shoot restraint 22 or the plant embryo 42, or both, may be contacted with a hydrated gel either before or after inserting the plant embryo 42 into the shoot restraint 22. Exemplary embodiments of hydrated gels are as described above for the nutritive media 26. The hydrated gel may comprise only gel solutes and water, or it may comprise plant nutrients and other substances, as described for the nutritive media 26.

The interior surface of the shoot restraint may be contacted with a hydrated gel solution that will cure to form a hydrated gel. A cavity 34 may then be made into the hydrated gel in the shoot restraint 22 and the plant embryo 42 inserted into the cavity 34 in the hydrated gel in the shoot restraint 22. In addition, or alternatively, at least a portion of the plant embryo 42 (such as the cotyledons) may be contacted with a hydrated gel solution that will cure to form a hydrated gel before inserting the plant embryo 42 into the shoot restraint 22.

As further shown in FIG. 1, in one embodiment of the invention, adsorbent material 80 either completely or partially surrounds the embryo 42 in the cavity 34 and increases the surface area of the embryo 42 in functional contact with the nutritive media 26, thereby providing multiple pathways for the nutrients from the nutritive media 26 to pass to the embryo 42. Suitable adsorbent materials include activated charcoal, Dowex resins, zeolites, alumina, clay, diatomaceous earth, silica gel, and Kieselguhr. During assembly of the manufactured seed 20, the adsorbent material 80 is deposited into the cavity 34 in any manner known in the art, including manually. The adsorbent material 80 is preferably, but not necessarily, deposited within the cavity 34 such that it substantially centers the plant embryo 42 within the cavity 34. Although it is preferred that the adsorbent material 80 substantially centers the plant embryo 42 within the cavity 34, the plant embryo 42 need not be so positioned. The adsorbent material 80 need only position the plant embryo 42 within the cavity 34 in any manner to place the plant embryo 42 into functional contact with the nutritive media 26. Further, it is not necessary for the adsorbent material 80 to "surround" the plant embryo 42. As such, the adsorbent material 80 can completely or partially surround the plant embryo 42. In other embodiments within the scope of the appended claims, the adsorbent material 80 need only fill, either completely or partially, one or two sides of the space between the plant embryo 42 and the walls of the cavity.

In one embodiment, the adsorbent material 80 in the cavity 34 is charcoal. Preferably, the charcoal is in the form of a powder and is activated by pretreatment with an acid such as HCl or phosphoric acid. Activated charcoal is commercially available. For example, powdered activated carbon NORIT® CNSP or DARCO® KB-G are available from Norit Americas Inc., Marshall, Tex. In another embodiment, the adsorbent material 80 in the cavity 34 is nutrient-treated charcoal. An exemplary method of preparing nutrient-treated charcoal for insertion into the cavity 34 is described in Example 2.

As used herein, a "plant embryo" refers to either a zygotic plant embryo or a somatic plant embryo. A zygotic plant embryo is an embryo found inside a botanic seed produced by sexual reproduction. Somatic embryos can be produced by culturing embryogenic tissue by standard methods under laboratory conditions in which the cells comprising the tissue are separated from one another and urged to develop into minute complete embryos.

As used herein, "a plant somatic embryo" refers to an embryo produced by culturing totipotent plant cells such as meristematic tissue under laboratory conditions in which the cells comprising the tissue are separated from one another and urged to develop into minute complete embryos. Alternatively, somatic embryos can be produced by inducing "cleavage polyembryogeny" of zygotic embryos. Methods for producing plant somatic embryos suitable for use in the methods of the invention are standard in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). For example, plant tissue may be cultured in an initiation media that includes hormones to initiate the formation of embryogenic cells, such as embryonic suspensor masses that are capable of developing into somatic embryos. The embryogenic cells may then be further cultured in a maintenance media that promotes establishment and multiplication of the embryogenic cells. Subsequently, the multiplied embryogenic cells may be cultured in a development media that promotes the development of somatic embryos, which may further be subjected to post-development treatments such as cold-treatments. The somatic embryos used in the methods of the invention have completed the development stage of the somatic embryogenesis process. They may also have been subjected to one or more post-development treatments.

Plant embryos suitable for use in the methods of the invention may be from any plant species, such as dicotyledonous or monocotyledonous plants, gymnosperms, etc. Conifer embryos suitable for use in the methods of the invention may be from conifer species, including, but not limited to, Loblolly pine embryos and Douglas fir embryos. For use in manufactured seeds 20 according to the present invention, the plant embryo 42 is typically developed sufficiently to have a shoot end and a radicle end. In certain species of plants, the shoot end includes one or more cotyledons in some stage of development. In other types of plants, the cotyledon(s) are situated in locations other than the shoot end.

In another aspect, the present invention provides methods for improving the germination of a plant embryo from a manufactured seed. In one embodiment, the method comprise the steps of (a) assembling a manufactured seed comprising a seed coat and a restraint, wherein the restraint comprises a cavity; (b) adding nutritive media comprising an adsorbent material, wherein the adsorbent material is present in the media in a concentration from about 30 g/L to about 100 g/L, to the seed coat; (c) placing a plant embryo into the cavity of the restraint; and (d) culturing the manufactured seed under conditions suitable for germination of the plant embryo. In one embodiment, the method comprise the steps of (a) assembling a manufactured seed comprising a seed coat and a restraint, wherein the restraint comprises a cavity; (b) adding nutritive media comprising an adsorbent material, wherein the adsorbent material is present in the media in a concentration from about 30 g/L to about 100 g/L, to the seed coat; (c) placing a plant embryo into the cavity of the restraint; (d) adding an adsorbent material to the cavity; and (e) culturing the manufactured seed under conditions suitable for germination of the plant embryo.

Conditions suitable for germination of manufactured seeds are standard in the art and include conditions suitable for germination of natural seeds. For example, the manufactured seeds may be sown in any of a variety of environments, such as in sand, vermiculite, sterile soil, and/or in the field (natural soil). For example, sterile Coles™ washed sand, which is available from a variety of gardening supply stores, may be used.

An exemplary method for assembling a plant embryo 42 into a manufactured seed 20 is described in Example 3.

The methods of the invention improve the germination of a plant embryo from a manufactured seed, as shown in Examples 4, 5, and 6.

The following examples are provided for the purpose of illustrating, not limiting, the invention.

EXAMPLES

Example 1

This example shows a representative method of preparation of a suitable nutritive media for use in the invention.

Nutritive Complete Media (KE64-50) is made by combining KE64 Basic Media (Table 1) with the components from Table 2, as described. KE64-50 is prepared from pre-made stocks. The required amount of each stock solution (that is not heat-labile) is added to water. Nonstock chemicals (such as charcoal and agar) are weighed out and added directly to the media. After all the nonheat-labile chemicals and compounds are added, the media is brought up to an appropriate volume and the pH is adjusted to 5.7. The media is then sterilized by autoclaving for 25 minutes.

TABLE 1

FORMULATION OF KE64 BASIC MEDIA

| Media Component | Final Concentration (mg/l) |
|---|---|
| $NH_4NO_3$ | 301.1 |
| $H_3BO_3$ | 10.0 |
| $(NH_4)_2MoO_4$ | 0.06 |
| $CaCl_2$—$2H_2O$ | 299.2 |
| $KH_2PO_4$ | 1800.0 |
| $MgSO_4$—$7H_2O$ | 1000.0 |
| $MnCl_2 \cdot 4H_2O$ | 6.0 |
| $ZnSO_4$—$7H_2O$ | 0.8 |
| $CuCl_2$—$2H_2O$ | 0.5 |
| Ferric Citrate | 60 |
| Pluronic F-68 | 10 g/l |
| Agar | 18 g/l |

Filter-sterilized heat-labile components (Table 2) are added after the media has cooled to 40° C.

TABLE 2

| Media Component | Final Concentration mM | Final Concentration (mg/l) |
|---|---|---|
| Myo-inositol | 0.5549 | 100.0 |
| Thiamine-HCl | 0.0030 | 1.0 |
| Pyridoxine-HCl | 0.0012 | 0.25 |
| Nicotinic acid | 0.0081 | 1.0 |
| Riboflavin | 0.0021 | 0.125 |
| Ca-pantothenate |  | 0.50 |
| Biotin | 0.0003 | 0.0010 |
| Folic acid | 0.8077 | 0.1250 |
| L-asparagine | 1.8255 | 106.7 |
| L-glutamine | 0.3646 | 266.7 |
| L-lysine-2HCl | 0.7612 | 53.3 |
| DL-serine | 0.4631 | 80 |
| L-proline | 1.5310 | 53.3 |
| L-arginine-HCl | 0.4552 | 266.7 |
| Urea | 13.3200 | 800 |
| L-valine | 0.5983 | 53.3 |
| L-alanine | 0.2203 | 53.3 |
| L-leucine | 0.2448 | 80 |
| L-threonine | 0.3226 | 26.7 |
| L-phenylalanine | 0.1720 | 53.3 |
| L-histidine | 0.1308 | 26.7 |
| L-tryptophan | 0.2035 | 26.7 |
| L-isoleucine | 1.2930 | 26.7 |
| L-methionine | 0.7100 | 26.7 |

TABLE 2-continued

| Media Component | Final Concentration mM | Final Concentration (mg/l) |
|---|---|---|
| L-glycine | 0.0003 | 53.3 |
| L-tyrosine | 0.2242 | 53.3 |
| L-cysteine | 0.6098 | 26.7 |
| Sucrose |  | 50 g/l |
| Gibberillic Acid ($GA_{4/7}$) |  | 0.1 |
| Antimicrobials |  | 1.0 ml/l |

Example 2

This example is a representative method of preparing nutrient-treated charcoal suitable for use in the invention. KE64 Basic Media (Table 1) is prepared as described in Example 1, without Pluronic F-68 and without agar. Nutrient-treated charcoal is prepared as follows: 23.3 grams of 100-mesh charcoal is added to 1 liter of KE64 Basic Media. The components are autoclaved and allowed to cool to 40° C. The components of Table 2, as described in Example 1, are added sterilely to the KE64 Basic Media and the media is stirred to mix the components. The media is filtered through Whatman #1 filter paper in a Buchner funnel to collect the charcoal. A moisture balance is used to determine the moisture content of the charcoal cake and the dry weight of the charcoal is calculated. If the nutrient-loaded charcoal is to be added to the cavity of the manufactured seed, it is first dried until it becomes flowable matter.

Example 3

This example is a representative method of assembling plant embryos into manufactured seeds and germinating manufactured seeds. In an exemplary method for preparing a manufactured seed for use in the invention, the seed coat is prepared by sectioning polycaprolactone tubing to the appropriate length. Ceramic shoot restraints are made by injecting a porcelain slip into a preformed mold with a pin in the center to create the shoot accepting cavity. The slip is allowed to dry to a consistency that allows removal of the preformed restraint. The restraint is subsequently heated to a temperature that allows the porcelain to form a porous, but fused structure. The restraint can be acid washed to remove impurities, if desired. Lids are made by pre-stretching Parafilm™ (Pechiney Plastic Packaging, Chicago, Ill. 60631).

Zygotic embryos are prepared from botanic seeds. The seeds are surface-sterilized by methods similar to those previously described (Cyr et al., Seed Sci. Res. 1:91-97 (1991)). The seeds are cracked open and the zygotic embryos are dissected from the megagametophyte with scalpel and forceps in a laminar flow hood.

Somatic embryos are produced according to standard methods previously described (see, e.g., U.S. Pat. Nos. 4,957, 866; 5,034,326; 5,036,007; 5,041,382; 5,236,841; 5,294,549; 5,482,857; 5,563,061; and 5,821,126). For example, plant tissue may be cultured in an initiation media that includes hormones to initiate the formation of embryogenic cells, such as embryonic suspensor masses that are capable of developing into somatic embryos. The embryogenic cells may then be further cultured in a maintenance media that promotes establishment and multiplication of the embryogenic cells. Subsequently, the multiplied embryogenic cells may be cultured in a development media that promotes the development of somatic embryos, which may further be subjected to post-development treatments such as cold treatments. The somatic embryos used in the methods of the invention have completed the development stage of the somatic embryogenesis process. They may also have been subjected to one or more post-development treatments.

Manufactured seed are assembled by thermobonding the ceramic shoot restraint 22 to the seed coat 24. The seed coat 24 is then filled with nutritive media 26 and an embryo is inserted into the cavity 34 in the cotyledon restraint 22, cotyledon end first. Dry charcoal fill material 80 (either nutrient-treated or non-nutrient-treated) may be loaded into the cotyledon restraint after the embryo is inserted into the cavity 34. After the charcoal has been added, the seeds are then sealed with a secondary end seal by laying it over the open end of the seed and fusing the lids to the surface with heat. The primary end seals are dipped into blue wax mixture prior to attaching the secondary end seal. This promotes good bonding between the primary and secondary end seals. The seeds are then swabbed with anti-microbial agents.

A suitable amount of sterile sand is prepared by baking 2 liters of sand at a temperature of 375° F. for 24 hours. The sand is then added to pre-sterilized trays and 285 ml water is added. Furrows are then formed and the box is sealed. The box containing the sand is then autoclaved for 1 hour at 121° C. and 1 atmospheric pressure.

The manufactured seeds are sown in the sand and allowed to germinate. Typically, the manufactured seeds are cultured under continuous light at room temperature (23° C.) for four to five weeks.

Example 4

This example shows a representative method of the invention for improving the germination of a plant embryo from a manufactured seed. Manufactured seeds were assembled as described in Example 3, subject to the variations described below, and zygotic Loblolly pine embryos were inserted into the seeds (one embryo per seed). In each experiment below, charcoal was added to the KE64 Basic Media, prepared as described in Example 1, before autoclaving. The concentration of charcoal in the media was 2.5 g/L; 60 g/L; or 100 g/L. In some treatments, the charcoal was nutrient-treated, as described in Example 2. In some treatments, the charcoal was not nutrient-treated. After autoclaving, the remainder of the components was added to prepare KE64 Complete Media.

Two different shoot restraints, Type A and Type B, were used in the treatments. In some treatments, charcoal was also added to the cavity in the shoot restraint. In some treatments, the charcoal added to the cavity was nutrient-treated. In some treatments, the charcoal added to the cavity was not nutrient treated. In some treatments, charcoal was not added to the cavity. The seeds were then allowed to germinate as described in Example 3. The treatments are described below.

| | Type A Shoot Restraint |
|---|---|
| Treatment 1: | KE64 Complete Media + 2.5 g/L non-nutrient-treated charcoal |
| Treatment 2: | KE64 Complete Media + 60 g/L non-nutrient-treated charcoal |
| Treatment 3: | KE64 Complete Media + 60 g/L nutrient-treated charcoal |
| Treatment 4: | KE64 Complete Media + 2.5 g/L non-nutrient-treated charcoal; and Nutrient-treated charcoal in the cavity |
| Treatment 5: | KE64 Complete Media + 60 g/L non-nutrient-treated charcoal; and Nutrient-treated charcoal in cavity |
| Treatment 6: | KE64 Complete Media + 60 g/L nutrient-treated charcoal; and Nutrient-treated charcoal in cavity |
| Treatment 7: | KE64 Complete Media + 2.5 g/L non-nutrient treated charcoal; and Non-nutrient-treated charcoal in cavity |
| | Type B Shoot Restraint |
| Treatment 8: | KE64 Complete Media + 2.5 g/L non-nutrient-treated charcoal; and Nutrient-treated charcoal in cavity |
| Treatment 9: | KE64 Complete Media + 60 g/L non-nutrient-treated charcoal; and Nutrient-treated charcoal in cavity |
| Treatment 10: | KE64 Complete Media + 60 g/L nutrient-treated charcoal; and Nutrient-treated charcoal in cavity |

Results

Data was collected at 28 days past sowing. Several parameters were measured to determine the effects of increasing the amount of charcoal in the nutritive media and/or adding charcoal to the cavity of the shoot restraint. The lengths of the radicle, hypocotyl, cotyledons, and epicotyl were measured. The term "radicle" refers to the part of a plant embryo that develops into the primary root of the resulting plant. The term "cotyledon" refers generally to the first, first pair, or first whorl (depending on the plant type) of leaf-like structures on the plant embryo that function primarily to make food compounds in the seed available to the developing embryo, but in some cases act as food storage or photosynthetic structures. The term "hypocotyl" refers to the portion of a plant embryo or seedling located below the cotyledons but above the radicle. The term "epicotyl" refers to the portion of the seedling stem that is above the cotyledons. The organ lengths were measured in centimeters and are shown in Table 3.

The germination rate was measured and is shown in Table 4. The normalcy of the germinants was also assessed and is shown in Table 5. The embryos were examined and classified as normal; would be normal if fully extracted from the cavity; not normal; fully extracted from the cavity, but not normal; and unchanged. The term "normal germinant" or "normalcy" denotes the presence of all expected parts of a plant at time of evaluation. In the case of gymnosperms, normalcy is characterized by the radicle having a length greater than 3 mm and no visibly discernable malformations compared to the appearance of embryos germinated from natural seed. "Not normal" means tissue on at least one organ is swollen, and the root and cotyledons are dead. "Not-normal fully extracted" means the germinant has fully emerged from the cavity but is not normal. "Unchanged" means embryo has not changed from day one of the experiment.

TABLE 3

| Treatment | | Radical $\alpha < 0.0001^1$ | Hypocotyl $\alpha = 0.2788$ | Cotyledon $\alpha = 0.1174$ | Epicotyl $\alpha = 0.2074$ |
|---|---|---|---|---|---|
| | Organ Lengths (measured in cm) | | | | |
| | Type A Restraint | | | | |
| 1 | Media: 2.5 g/L non-nutrient-treated charcoal<br>Cavity: No charcoal | $1.03^B$ | 2.02 | 1.16 | 0.43 |
| 2 | Media: 60 g/L non-nutrient-treated charcoal<br>Cavity: No charcoal | $1.35^B$ | 3.81 | 1.26 | 0.43 |
| 3 | Media: 60 g/L Nutrient-treated charcoal<br>Cavity: No charcoal | $1.46^{B,D}$ | 2.21 | 1.3 | 0.43 |
| 4 | Media: 2.5 g/L non-nutrient-treated charcoal<br>Cavity: Nutrient-treated charcoal | $1.14^{B,C}$ | 1.91 | 1.21 | |
| 5 | Media: 60 g/L non-nutrient-treated charcoal<br>Cavity: Nutrient-treated charcoal | $1.34^{B,C,D}$ | 2.46 | 1.32 | 0.13 |
| 6 | Media: 60 g/L Nutrient-treated charcoal<br>Cavity: Nutrient-treated charcoal | $1.54^{A,B,C,D}$ | 2.71 | 1.41 | 0.52 |
| 7 | Media: 2.5 g/L non-nutrient-treated charcoal<br>Cavity: Non-nutrient-treated charcoal | $1.94^{A,C,D}$ | 2.63 | 1.77 | 0.28 |
| | Type B Restraint | | | | |
| 8 | Media: 2.5 g/L Non-nutrient-treated charcoal<br>Cavity: Nutrient-treated charcoal | $1.89^{A,B,C}$ | 2.52 | 1.42 | 0.42 |
| 9 | Media: 60 g/L Non-nutrient-treated charcoal<br>Cavity: Nutrient-treated charcoal | $2.20^{A,D}$ | 2.88 | 1.47 | 0.16 |
| 10 | Media: 60 g/L Nutrient-treated charcoal<br>Cavity: Nutrient-treated charcoal | $2.32^A$ | 2.62 | 1.55 | 0.16 |

[1] Means followed by the same letter not significantly different

TABLE 4

| Treatment | | Above[1] $\alpha = 0.1310$ | Partial[2] $\alpha = 0.6100$ | Below[3] $\alpha = 0.0022$ | Upside down[4] $\alpha = 0.3457$ |
|---|---|---|---|---|---|
| | Germination Rate | | | | |
| | Type A Restraint | | | | |
| 1 | Media: 2.5 g/L non-nutrient-treated charcoal<br>Cavity: No charcoal | 13.9% | 19.4% | 55.6% | 8.3% |
| 2 | Media: 60 g/L non-nutrient-treated charcoal<br>Cavity: No charcoal | 41.7% | 22.2% | 27.8% | 5.6% |
| 3 | Media: 60 g/L Nutrient-treated charcoal<br>Cavity: No charcoal | 36.1% | 11.1% | 44.4% | 2.8% |
| 4 | Media: 2.5 g/L non-nutrient-treated charcoal<br>Cavity: Nutrient-treated charcoal | 11.1% | 8.3% | 77.8% | 0% |
| 5 | Media: 60 g/L non-nutrient-treated charcoal<br>Cavity: Nutrient-treated charcoal | 22.2% | 16.7% | 55.6% | 5.6% |
| 6 | Media: 60 g/L Nutrient-treated charcoal<br>Cavity: Nutrient-treated charcoal | 19.4% | 16.7% | 61.1% | 0% |
| 7 | Media: 2.5 g/L non-nutrient-treated charcoal<br>Cavity: Non-nutrient-treated charcoal | 30.6% | 33.3% | 30.6% | 2.8% |

TABLE 4-continued

| | | Germination Rate | | | |
|---|---|---|---|---|---|
| Treatment | | Above[1] $\alpha = 0.1310$ | Partial[2] $\alpha = 0.6100$ | Below[3] $\alpha = 0.0022$ | Upside down[4] $\alpha = 0.3457$ |
| | Type B Restraint | | | | |
| 8 | Media: 2.5 g/L Non-nutrient-treated charcoal Cavity: Nutrient-treated charcoal | 38.9% | 27.8% | 30.6% | 0% |
| 9 | Media: 60 g/L Non-nutrient-treated charcoal Cavity: Nutrient-treated charcoal | 36.1% | 25% | 36.1% | 2.8% |
| 10 | Media: 60 g/L Nutrient-treated charcoal Cavity: Nutrient-treated charcoal | 33.3% | 25% | 36.1% | 2.8% |

[1] "Above" means cotyledons and hypocotyl above ground
[2] "Partial" means some green tissue showing above ground
[3] "Below" means nothing showing above ground
[4] "Upside Down" means root has died and the hypocotyl is turned up into the air

TABLE 5

| | | Normalcy | | | | |
|---|---|---|---|---|---|---|
| Treatment | | Normal $\alpha = 0.0206$ | Would be normal if fully extracted $\alpha = 0.1325$ | Not normal $\alpha = 0.6576$ | Fully extracted, not normal $\alpha = 0.4540$ | Unchanged $\alpha = 0.1064$ |
| | TYPE A Restraint | | | | | |
| 1 | Media: 2.5 g/L non-nutrient-treated charcoal Cavity: No charcoal | 13.9% | 5.6% | 27.8% | 5.6% | 44.4% |
| 2 | Media: 60 g/L non-nutrient-treated charcoal Cavity: No charcoal | 36.1% | 19.4% | 25% | 0% | 19.4% |
| 3 | Media: 60 g/L Nutrient-treated charcoal Cavity: No charcoal | 36.1% | 5.6% | 25% | 0% | 27.8% |
| 4 | Media: 2.5 g/L non-nutrient-treated charcoal Cavity: Nutrient-treated charcoal | 8.3% | 8.3% | 25% | 0% | 58.3% |
| 5 | Media: 60 g/L non-nutrient-treated charcoal Cavity: Nutrient-treated charcoal | 16.7% | 8.3% | 36.1% | 0% | 36.1% |
| 6 | Media: 60 g/L Nutrient-treated charcoal Cavity: Nutrient-treated charcoal | 16.7% | 13.9% | 16.7% | 0% | 50% |
| 7 | Media: 2.5 g/L non-nutrient-treated charcoal Cavity: Non-nutrient-treated charcoal | 33.3% | 22.2% | 19.4% | 2.8% | 22.2% |
| | Type B Restraint | | | | | |
| 8 | Media: 2.5 g/L Non-nutrient-treated charcoal Cavity: Nutrient-treated charcoal | 36.1% | 16.7% | 13.9% | 0% | 27.8% |
| 9 | Media: 60 g/L Non-nutrient-treated charcoal | 41.7% | 8.3% | 13.9% | 2.8% | 33.3% |

TABLE 5-continued

| | Treatment | Normal<br>$\alpha = 0.0206$ | Would be normal if fully extracted<br>$\alpha = 0.1325$ | Not normal<br>$\alpha = 0.6576$ | Fully extracted, not normal<br>$\alpha = 0.4540$ | Unchanged<br>$\alpha = 0.1064$ |
|---|---|---|---|---|---|---|
| 10 | Cavity: Nutrient-treated charcoal<br>Media: 60 g/L Nutrient-treated charcoal<br>Cavity: Nutrient-treated charcoal | 27.8% | 30.6% | 16.7% | 0% | 25% |

The data in Tables 3, 4, and 5 generally shows an increase in organ length, germination rate, and normalcy in embryos germinated from manufactured seed in which the nutritive media includes a high level of charcoal (60 g/L versus 2.5 g/L).

Example 5

This example shows a representative method of the invention for improving the germination of a plant embryo from a manufactured seed. Manufactured seeds were assembled as described in Example 3, subject to the variations described below, and zygotic Loblolly pine embryos were inserted into the seeds (one embryo per seed). In each treatment below, charcoal was added to the KE64 Basic Media, prepared as described in Example 1, before autoclaving. The concentration of charcoal in the media was 0 g/L; 60 g/L; or 100 g/L. In some treatments, the charcoal was nutrient-treated, prepared as described in Example 2. In some treatments, the charcoal was not nutrient-treated. After autoclaving, the remainder of the components was added to prepare KE64 Complete Media.

Only Type B shoot restraints were used in the treatments. In all treatments, nutrient-treated charcoal was added to the cavity in the shoot restraint. The seeds were then allowed to germinate as described in Example 3. The treatments are described below.

| | |
|---|---|
| Treatment 1: | KE64 Complete Media; and Nutrient-treated charcoal in the cavity |
| Treatment 2: | KE64 Complete Media + 60 g/L non-nutrient-treated charcoal; and Nutrient-treated charcoal in the cavity |
| Treatment 3: | KE64 Complete Media + 60 g/L nutrient-treated charcoal; and Nutrient-treated charcoal in cavity |
| Treatment 4: | KE64 Complete Media + 100 g/L non-nutrient-treated charcoal; and Nutrient-treated charcoal in the cavity |
| Treatment 5: | KE64 Complete Media + 100 g/L nutrient-treated charcoal; and Nutrient-treated charcoal in cavity |

Results

Data was collected at 41 days past sowing. Several parameters were measured to determine the effects of increasing the amount of charcoal in the nutritive media and adding charcoal to the cavity of the shoot restraint. Organ lengths were measured and germination rate and normalcy were determined. Terms are defined as in Example 4. Organ lengths are shown in Table 6, germination rate is shown in Table 7, and normalcy is shown in Table 8.

TABLE 6

| | Treatment | | Radical<br>$\alpha = 0.0200$ | Hypocotyl<br>$\alpha = 0.0192$ | Cotyledon<br>$\alpha = 0.1183$ | Epicotyl<br>$\alpha = 0.0415$ |
|---|---|---|---|---|---|---|
| 1 | Media: No charcoal<br>Cavity: Nutrient-treated charcoal | | $1.95^B$ | $2.41^B$ | 1.44 | $0.37^B$ |
| 2 | Media: 60 g/L non-nutrient-treated charcoal<br>Cavity: Nutrient-treated charcoal | | $2.57^{AB}$ | $2.62^{AB}$ | 1.55 | $0.43^{AB}$ |
| 3 | Media: 60 g/L nutrient-treated charcoal<br>Cavity: Nutrient-treated charcoal | | $2.74^{AB}$ | $2.98^A$ | 1.69 | $0.41^{AB}$ |
| 4 | Media: 100 g/L non-nutrient-treated charcoal<br>Cavity: Nutrient-treated charcoal | | $2.56^{AB}$ | $2.78^{AB}$ | 1.75 | $0.62^A$ |

TABLE 6-continued

Organ Lengths (measured in cm)

| Treatment | | Radical $\alpha = 0.0200$ | Hypocotyl $\alpha = 0.0192$ | Cotyledon $\alpha = 0.1183$ | Epicotyl $\alpha = 0.0415$ |
|---|---|---|---|---|---|
| 5 | Media: 100 g/L Nutrient-treated charcoal<br>Cavity: Nutrient-treated charcoal | 2.99$^A$ | 2.70$^{AB}$ | 1.61 | 0.50$^{AB}$ |

TABLE 7

Germination Rate

| Treatment | | Above $\alpha = 0.0345$ | Partial $\alpha = 0.0192$ | Below $\alpha = 0.1183$ | Upside Down $\alpha = 0.0415$ |
|---|---|---|---|---|---|
| 1 | Media: No charcoal<br>Cavity: Nutrient-treated charcoal | 57.4%$^B$ | 22.4% | 10% | 10.2%$^A$ |
| 2 | Media: 60 g/L non-nutrient-treated charcoal<br>Cavity: Nutrient-treated charcoal | 57.1%$^B$ | 31.4% | 10% | 1.4%$^B$ |
| 3 | Media: 60 g/L nutrient- treated charcoal<br>Cavity: Nutrient-treated charcoal | 77.6%$^A$ | 15.7%$^A$ | 5.2% | 1.4%$^B$ |
| 4 | Media: 100 g/L non-nutrient-treated charcoal<br>Cavity: Nutrient-treated charcoal | 58.6%$^{AB}$ | 34.3% | 4.3% | 2.9%$^B$ |
| 5 | Media: 100 g/L Nutrient- treated charcoal<br>Cavity: Nutrient-treated charcoal | 72.5%$^{AB}$ | 20.3% | 4.3% | 2.9%$^B$ |

TABLE 8

Normalcy

| Treatment | | Normal $\alpha = 0.0345$ | Would be Normal if fully extracted $\alpha = 0.0192$ | Not Normal $\alpha = 0.1183$ | Unchanged $\alpha = 0.0415$ |
|---|---|---|---|---|---|
| 1 | Media: No charcoal<br>Cavity: Nutrient-treated charcoal | 65.9% $^B$ | 8.3% | 20.8% | 5.6% |
| 2 | Media: 60 g/L non-nutrient-treated charcoal<br>Cavity: Nutrient-treated charcoal | 72.9%$^{AB}$ | 8.6% | 12.9% | 5.7% |
| 3 | Media: 60 g/L nutrient-treated charcoal<br>Cavity: Nutrient-treated charcoal | 80.5%$^{AB}$ | 10.0%$^A$ | 6.7% | 2.9% |
| 4 | Media: 100 g/L non-nutrient-treated charcoal<br>Cavity: Nutrient-treated charcoal | 72.9%$^{AB}$ | 17.1% | 8.6% | 0.0% |
| 5 | Media: 100 g/L Nutrient-treated charcoal<br>Cavity: Nutrient-treated charcoal | 84.3% $^A$ | 7.1% | 4.3% | 4.3% |

The data in Tables 6, 7, and 8 shows an increase in organ length, germination rate, and normalcy in embryos germinated from manufactured seed in which the nutritive media includes a high level of charcoal (60 g/L versus 0 g/L). The data in Table 7 also shows a decreased rate of "upside down" germinants as the amount of charcoal in the media is increased.

Example 6

This example shows a representative method of the invention for improving the germination of a plant embryo from a manufactured seed. Manufactured seeds were assembled as described in Example 3, subject to the variations described below, and zygotic Loblolly pine embryos were inserted into the seeds (one embryo per seed). In each experiment below, charcoal was added to the KE64 Basic Media, prepared as described in Example 1, before autoclaving. The Basic Media was brought up to volume before adding the charcoal. The concentration of charcoal in the media was 0 g/L; 3 g/L; 30 g/L; 50 g/L; 60 g/L; 75 g/L; or 100 g/L. In all the experiments, the charcoal was nutrient-treated, prepared as described in Example 2, except no sucrose was added to KE64 Basic Media when preparing the nutrient-treated charcoal for this experiment. After autoclaving, the remainder of the components was added to prepare KE64 Complete Media (II), which differs from KE64 Complete Media in that the concentration of sucrose is 63.5 g/L.

Only Type A shoot restraints were used in the experiments. In all treatments, nutrient-treated charcoal was added to the cavity in the shoot restraint. The seeds were then allowed to germinate as described in Example 3. The treatments are described below. Each treatment was performed on average with 60 seeds per treatment.

Treatment 1: KE64 Complete Media (II)+100 g/L nutrient-treated charcoal

Treatment 2: KE64 Complete Media (II)+75 g/L nutrient-treated charcoal

Treatment 3: KE64 Complete Media (II)+60 g/L nutrient-treated charcoal

Treatment 4: KE64 Complete Media (II)+50 g/L nutrient-treated charcoal

Treatment 5: KE64 Complete Media (II)+30 g/L nutrient-treated charcoal

Treatment 6: KE64 Complete Media (II)+3 g/L nutrient-treated charcoal

Treatment 7: KE64 Complete Media (II)+0 g/L nutrient-treated charcoal

Results

Figure 3:
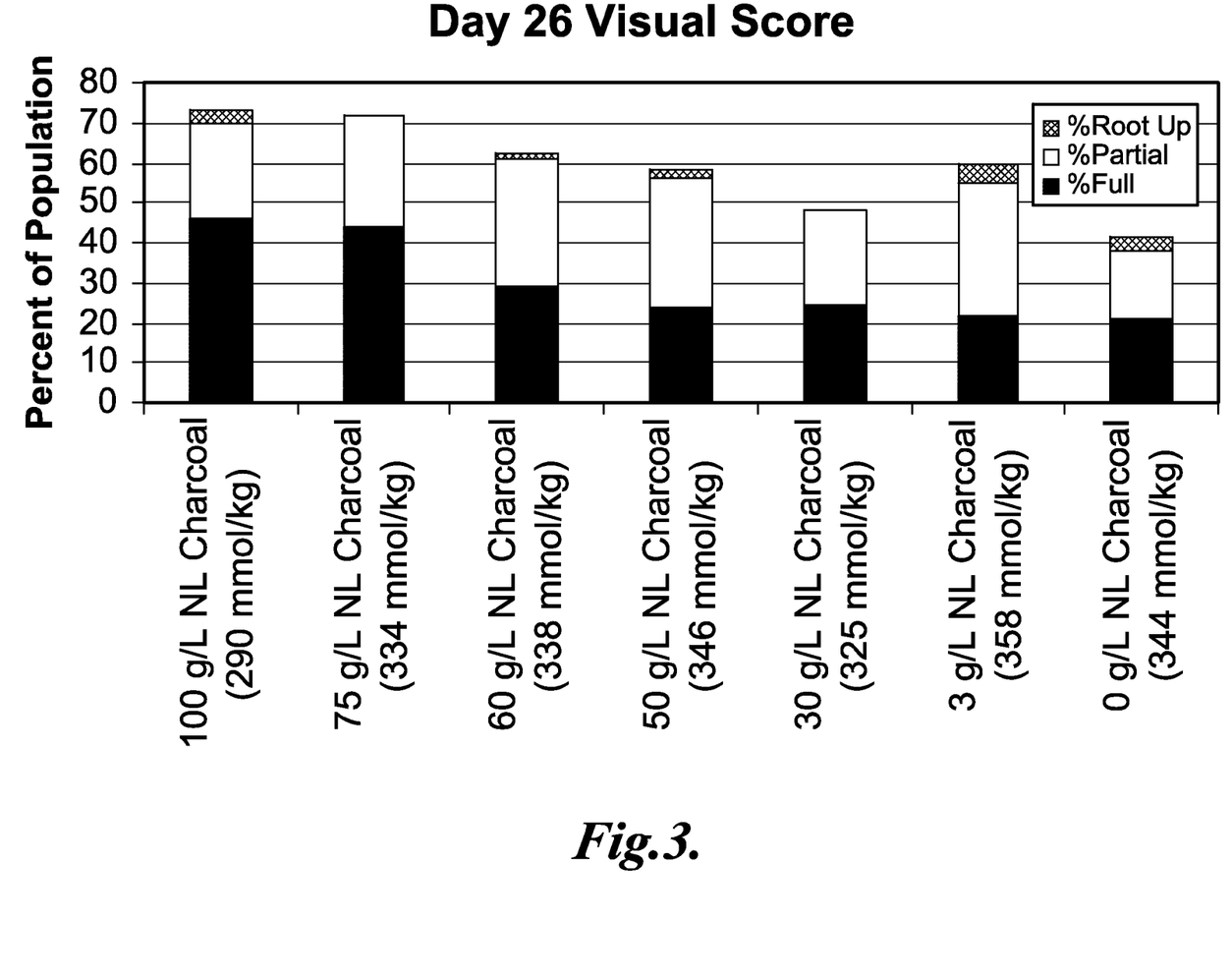
FIG. 3 is a graph illustrating the rates of germination of embryos disposed in a manufactured seed having increasing amounts of charcoal in the nutritive media. Observations were made 26 days after sowing.
Figure 4:
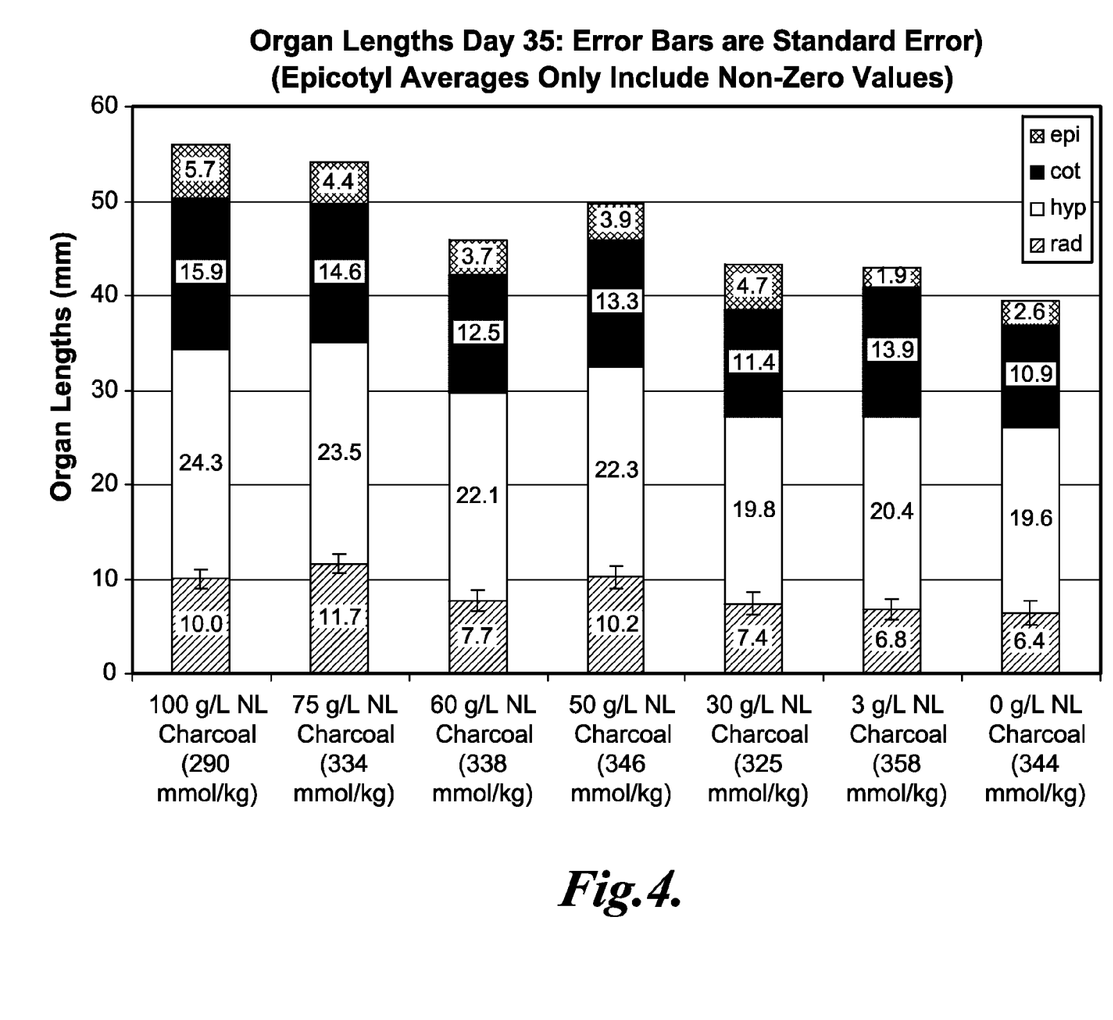
FIG. 4 is a graph illustrating organ lengths of embryos disposed in a manufactured seed having increasing amounts of charcoal in the nutritive media. Observations were made 35 days after sowing.
Figure 5:
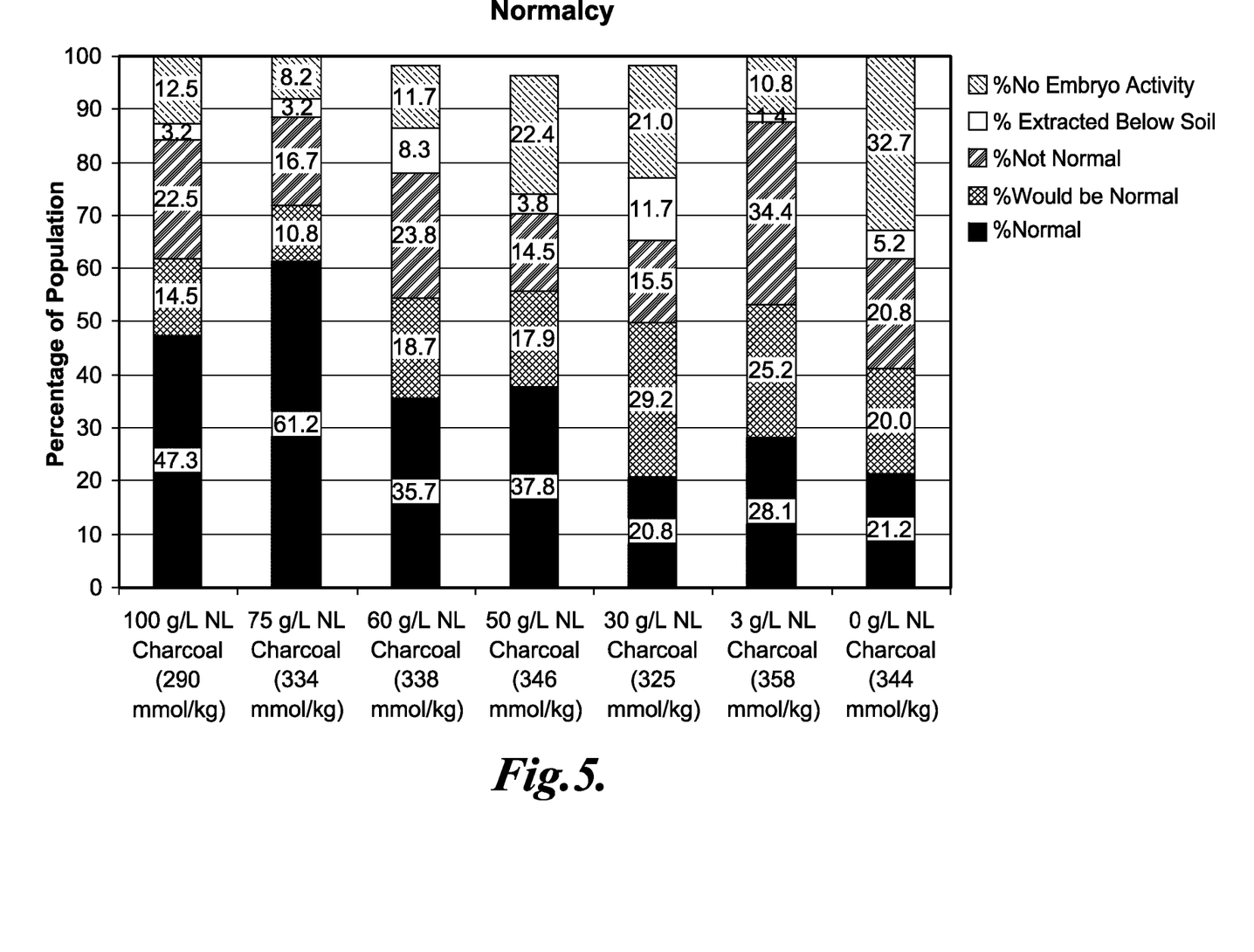
FIG. 5 is a graph illustrating the incidence of embryos disposed in a manufactured seed having increasing amounts of charcoal in the nutritive media. Observations were made 35 days after sowing.

Data was collected at 19, 26, and 35 days past sowing. Several parameters were measured to determine the effects of increasing the amount of charcoal in the nutritive media and adding charcoal to the cavity of the shoot restraint. Organ lengths were measured and germination rate and normalcy were determined. Terms are defined as in Example 4. Germination rate is shown in FIGS. 2 and 3; organ lengths are shown in FIG. 4; and normalcy incidence is shown in FIG. 5.

Figure 2:
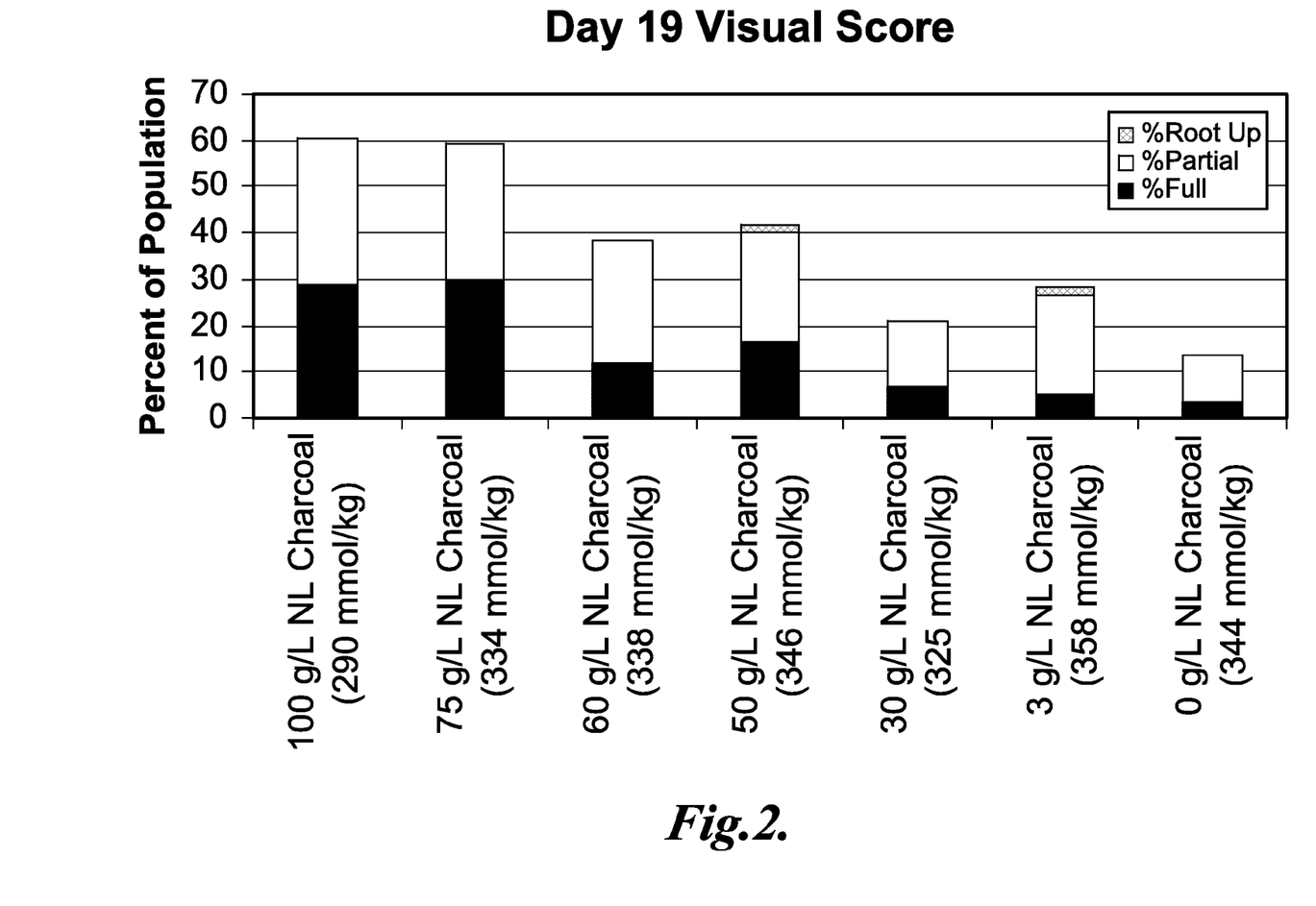
FIG. 2 is a graph illustrating the rates of germination of embryos disposed in a manufactured seed having increasing amounts of charcoal in the nutritive media. Observations were made 19 days after sowing.

At day 19, embryos in seeds with higher charcoal content in the nutritive media showed faster germination than seeds with lower charcoal (FIG. 2). At day 26, the seeds with higher charcoal content maintained a faster germination rate (FIG. 3). In addition, organ lengths were generally greater in embryos in seeds with greater charcoal in the nutritive media (FIG. 4). Finally, normalcy data showed greater incidence of normal germinants from embryos in seeds with greater charcoal in the nutritive media (FIG. 5). Conversely, inactive embryos and germinants that would be normal if fully extracted increased with decreasing charcoal. These data suggest that increased charcoal in the nutritive media provides improved performance to embryos in manufactured seed.

While illustrative embodiments have been illustrated and described, it will be appreciated that various changes can be made therein without departing from the spirit and scope of the invention.

The embodiments of the invention in which an exclusive property or privilege is claimed are defined as follows:

1. A manufactured seed comprising:
   a seed coat;
   a nutritive media comprising an adsorbent material, wherein the adsorbent material is present in the nutritive media in a concentration from about 50 g/L to about 100 g/L, and wherein the adsorbent material is selected from the group consisting of charcoal, polyvinyl polypyrolidone, and silica gels; and
   a shoot restraint, wherein the seed coat contacts the shoot restraint and wherein the shoot restraint comprises a cavity, and wherein the nutritive medium contacts an outer surface of the shoot restraint and an inner surface of the seed coat.

2. The manufactured seed of claim 1, wherein the adsorbent material is silica gels.

3. The manufactured seed of claim 1, wherein the adsorbent material is charcoal.

4. The manufactured seed of claim 3, wherein the charcoal is present in the media in a concentration from about 60 g/L to about 100 g/L.

5. The manufactured seed of claim 3, wherein the charcoal is nutrient treated.

6. The manufactured seed of claim 3, wherein the charcoal is non nutrient treated.

7. The manufactured seed of claim 1, further comprising a plant embryo disposed in the cavity of the shoot restraint.

8. The manufactured seed of claim 7, wherein the adsorbent material is disposed within the cavity of the shoot restraint.

9. The manufactured seed of claim 8, wherein the adsorbent material within the cavity is charcoal.

10. The manufactured seed of claim 9, wherein the charcoal is nutrient treated.

11. The manufactured seed of claim 9, wherein the charcoal is non nutrient treated.

12. A method for germination of a plant embryo from a manufactured seed comprising:
    assembling a manufactured seed comprising a seed coat and a shoot restraint, wherein the seed coat contacts the shoot restraint, and wherein the shoot restraint comprises a cavity;
    adding nutritive media comprising an adsorbent material, wherein the adsorbent material is present in the media in a concentration from about 50 g/L to about 100 g/L, and wherein the adsorbent material is selected from the group consisting of charcoal, polyvinyl polypyrolidone, and silica gels, to fill the seed coat, wherein the nutritive media contacts an inner surface of the seed coat and an outer surface of the shoot restraint, and;
    placing a plant embryo into the cavity of the shoot restraint; and
    culturing the manufactured seed under conditions suitable for germination of the plant embryo.

13. The method of claim 12, wherein the adsorbent material is silica gels.

14. The method of claim 12, wherein the adsorbent material is charcoal.

15. The method of claim 14, wherein the charcoal is nutrient treated.

16. The method of claim 14, wherein the charcoal is non nutrient treated.

17. The method of claim 12, further comprising adding the adsorbent material to the cavity of the shoot restraint.

18. The method of claim 17, wherein the adsorbent material added to the cavity is silica gels.

19. The method of claim 17, wherein the adsorbent material added to the cavity is charcoal.

20. The method of claim 19, wherein the charcoal added to the cavity is nutrient treated.

* * * * *